US012778459B2

(12) United States Patent
Khan et al.

(10) Patent No.: US 12,778,459 B2
(45) Date of Patent: Nov. 3, 2026

(54) ELECTRONIC APPARATUS AND CONTROLLING METHOD THEREOF

(71) Applicant: Samsung Electronics Co., Ltd., Suwon-si (KR)

(72) Inventors: Faisal Khan, Dacca (BD); Ibraheem Muhammad Moosa, Dacca (BD); Md. Mahmud Muntakim Khan, Dacca (BD)

(73) Assignee: Samsung Electronics Co., Ltd., Suwon-si (KR)

( * ) Notice: Subject to any disclaimer, the term of this patent is extended or adjusted under 35 U.S.C. 154(b) by 35 days.

(21) Appl. No.: 18/663,600

(22) Filed: May 14, 2024

(65) Prior Publication Data

US 2024/0298927 A1 Sep. 12, 2024

Related U.S. Application Data

(63) Continuation of application No. PCT/KR2022/018884, filed on Nov. 25, 2022.

(30) Foreign Application Priority Data

Nov. 26, 2021 (KR) ........................ 10-2021-0166188

(51) Int. Cl.
*G06F 21/32* (2013.01)
*A61B 5/00* (2006.01)
(Continued)

(52) U.S. Cl.
CPC .......... *A61B 5/1172* (2013.01); *A61B 5/0205* (2013.01); *A61B 5/7203* (2013.01); *A61B 5/7246* (2013.01); *A61B 5/024* (2013.01)

(58) Field of Classification Search
CPC ... A61B 5/1172; A61B 5/0205; A61B 5/7203; A61B 5/7246; A61B 5/024
See application file for complete search history.

(56) References Cited

U.S. PATENT DOCUMENTS 9,223,956 B2 * 12/2015 Hong .................... H04W 12/33
9,396,642 B2 * 7/2016 He ..................... A61B 5/02108
(Continued)

FOREIGN PATENT DOCUMENTS

JP 2017-070739 A 4/2017
KR 10-2015-0014788 A 2/2015
(Continued)

OTHER PUBLICATIONS

International Search Report dated Mar. 24, 2023, issued in International Patent Application No. PCT /KR2022/018884.
(Continued)

*Primary Examiner* — Quang Pham
(74) *Attorney, Agent, or Firm* — Jefferson IP Law, LLP

(57) ABSTRACT

A method of controlling an electronic apparatus is provided. The method includes based on a user touch for a first pulse wave sensor included in the electronic apparatus being detected, obtaining a first pulse wave signal through the first pulse wave sensor and receiving a second pulse wave signal detected through a second pulse wave sensor included in a wearable device from the wearable device, removing noise of the first pulse wave signal and the second pulse wave signal using a band pass filter, obtaining a cross-correlation signal indicating a correlation between denoised first pulse wave signal and the denoised second pulse wave signal, and authenticating a user based on the cross-correlation signal.

16 Claims, 12 Drawing Sheets

(51) Int. Cl.

| | |
|---|---|
| ***A61B 5/0205*** | (2006.01) |
| ***A61B 5/1172*** | (2016.01) |
| ***G07C 9/26*** | (2020.01) |
| ***G07C 9/37*** | (2020.01) |
| *A61B 5/024* | (2006.01) |

(56) References Cited

U.S. PATENT DOCUMENTS 9,558,336 B2 * 1/2017 Lee ........................ A61B 5/349
9,600,064 B2 * 3/2017 Lee ........................ G06V 40/16
9,811,648 B2 * 11/2017 Choi .................... H04W 12/065
10,159,444 B2 * 12/2018 Lin ...................... A61B 5/7246
10,248,779 B2 * 4/2019 Song .................. G06Q 20/3223
10,390,225 B2 * 8/2019 Mao ...................... H04L 63/107
10,448,848 B2 * 10/2019 Park .................... A61B 5/0022
10,699,558 B2 * 6/2020 Chang ...................... A61B 5/08
10,868,693 B2 * 12/2020 Lee ...................... A61M 21/02
11,496,723 B1 * 11/2022 Nepveu ................ G06T 19/006
11,531,736 B1 * 12/2022 Sun ........................ G10L 17/00
12,204,624 B2 * 1/2025 Lee ........................ G06F 21/32
12,311,882 B2 * 5/2025 Kim ....................... B60R 25/25
12,511,359 B2 * 12/2025 Hinatsu .................. G06F 21/32
2016/0042166 A1 * 2/2016 Kang .................. G06F 3/04886 726/7
2016/0061472 A1 * 3/2016 Lee ......................... F24F 11/64 700/276
2016/0070899 A1 * 3/2016 Vemula ................ G06F 21/606 726/19
2016/0106320 A1 * 4/2016 Shimuta ............... A61B 5/0205 600/301
2016/0196635 A1 * 7/2016 Cho .......................... G06T 3/40 345/660
2016/0227009 A1 * 8/2016 Kim ....................... B60K 35/10
2016/0322078 A1 * 11/2016 Bose .................. A63B 24/0003
2016/0342781 A1 * 11/2016 Jeon ................... G06V 40/1365
2016/0367138 A1 * 12/2016 Kim ..................... A61B 5/6898
2017/0115755 A1 * 4/2017 Jung .................... A61B 5/0205
2017/0116402 A1 * 4/2017 Hirabayashi ............ G06F 21/31
2017/0146387 A1 * 5/2017 Wiard .................... G01G 19/50
2017/0193208 A1 * 7/2017 Ashley .................... G06F 21/32
2017/0228631 A1 * 8/2017 Larsen ............. G06K 19/07354
2017/0243359 A1 * 8/2017 Bose ..................... A63F 13/212
2017/0286748 A1 * 10/2017 Kim ................... G06V 40/1382
2017/0323166 A1 * 11/2017 Colussi ............ G06K 19/07354
2018/0018454 A1 * 1/2018 Parry ...................... H04L 63/10
2018/0020194 A1 * 1/2018 Kim ....................... H04N 7/188
2019/0230507 A1 * 7/2019 Li ......................... H04W 12/06
2019/0246991 A1 * 8/2019 Choi ...................... A61B 5/145
2019/0274565 A1 * 9/2019 Soli .................... A61B 5/02438
2019/0298224 A1 * 10/2019 Rahman ............... A61B 5/6898
2019/0332757 A1 * 10/2019 Chen ...................... G06V 40/45
2020/0064921 A1 * 2/2020 Kang ..................... A61B 5/377
2020/0196920 A1 * 6/2020 Vaddiraju .......... A61B 5/14546
2020/0302146 A1 * 9/2020 Bjerre ................... G06F 3/0487
2020/0359922 A1 * 11/2020 Genicot ............... A61B 5/0245
2020/0410191 A1 * 12/2020 Skovgaard Christensen ............... G06F 3/0445
2021/0085216 A1 * 3/2021 Peters .................... G16H 40/67
2021/0128062 A1 * 5/2021 Karimli ................ A61B 5/4884
2021/0134469 A1 * 5/2021 Park ...................... A61B 5/1118
2021/0153757 A1 * 5/2021 Jeon ..................... A61B 5/7257
2021/0192920 A1 * 6/2021 Stenlund ................. B60R 25/01
2021/0212581 A1 * 7/2021 Kim ................... A61B 5/14532
2021/0274454 A1 * 9/2021 Ban ........................ A61B 5/002
2021/0290081 A1 * 9/2021 Clifton-Climas ......... G01T 7/00
2021/0319782 A1 * 10/2021 Gong ...................... G06F 3/167
2021/0334346 A1 * 10/2021 Sim ......................... G06F 21/32
2022/0031176 A1 * 2/2022 Redtel ................ A61B 5/02156
2022/0114245 A1 * 4/2022 Krishan .................. G06F 21/32
2022/0135003 A1 * 5/2022 Lee .................. G06Q 20/40145 701/2
2022/0172544 A1 * 6/2022 Kochi ..................... G06F 21/32
2022/0216996 A1 * 7/2022 Taylor ................... H04L 9/0866
2022/0249027 A1 * 8/2022 Chung ................. A61B 5/0077
2023/0086442 A1 * 3/2023 Van Ostrand ...... G06V 40/1306 345/173
2023/0130790 A1 * 4/2023 Pallerla ................... G06F 18/22 382/124
2025/0087014 A1 * 3/2025 Hassan .................. G06V 40/40
2025/0252171 A1 * 8/2025 Hinatsu .................. G06V 40/28

FOREIGN PATENT DOCUMENTS

KR 10-2015-0068694 A 6/2015
KR 10-2015-0112621 A 10/2015
KR 10-2016-0075677 A 6/2016
KR 10-1711835 B1 2/2017
KR 10-1826300 B1 1/2018
KR 10-1924702 B1 11/2018
KR 10-2020-0127437 A 11/2020
KR 10-2510543 B1 3/2023
WO 2015/127142 A1 8/2015
WO 2017/132061 A1 8/2017
WO WO-2019208923 A1 * 10/2019 ............... G06F 1/16

OTHER PUBLICATIONS

Extended European Search Report dated Dec. 6, 2024, issued in European Patent Application No. 22899099.0.

Korean Office Action dated Sep. 15, 2025, issued in Korean Patent Application No. 10-2021-0166188.

European Notice of Allowance dated Feb. 16, 2026, issued in European Application No. 22899099.0.

* cited by examiner

WHEN USER AUTHENTICATION IS FAILED

WHEN USER AUTHENTICATION IS SUCCESSFUL

ELECTRONIC APPARATUS AND CONTROLLING METHOD THEREOF

CROSS-REFERENCE TO RELATED APPLICATION(S)

This application is a continuation application, claiming priority under § 365(c), of an International application No. PCT/KR2022/018884, filed on Nov. 25, 2022, which is based on and claims the benefit of a Korean patent application number 10-2021-0166188, filed on Nov. 26, 2021, in the Korean Intellectual Property Office, the disclosure of which is incorporated by reference herein in its entirety.

BACKGROUND

1. Field

This disclosure relates to an electronic apparatus and a method of controlling thereof. More particularly, the disclosure relates to an electronic apparatus that authenticates a user using a pulse wave signal obtained from the user and a method of controlling thereof.

2. Description of Related Art

With the development of technology, the functions that can be performed by an electronic apparatus are becoming more diverse, and the time a user spends using an electronic apparatus and the amount of power consumed by the electronic apparatus are also increasing. Accordingly, various technologies for reducing power consumption of an electronic apparatus are continuously being developed, but there is an issue that the technologies developed to date do not sufficiently reflect the user's usage environment or behavior.

In a user authentication system, an electronic apparatus can authenticate a user based on authentication information provided by the user.

In this case, the authentication information may include a password entered by the user or the user's biometric information. Biometric information includes information regarding a fingerprint, iris or face.

However, there is an issue in that an unauthorized user neutralizes the user authentication system of the electronic apparatus in various ways, such as imitating the user's biometric information.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide an electronic apparatus that authenticates a user by comparing biometric information obtained from a wearable device worn by the user and biometric information obtained by the electronic apparatus and a method of controlling thereof.

Additional aspects will be set forth in part in the description which follows and, in part, will be apparent from the description, or may be learned by practice of the presented embodiments.

In accordance with an aspect of the disclosure, a method of controlling an electronic apparatus is provided. The method includes, based on a user touch for a first pulse wave sensor included in the electronic apparatus being detected, obtaining a first pulse wave signal through the first pulse wave sensor and receiving a second pulse wave signal detected through a second pulse wave sensor included in a wearable device from the wearable device, removing noise of the first pulse wave signal and the second pulse wave signal using a band pass filter, obtaining a cross-correlation signal indicating a correlation between denoised first pulse wave signal and the denoised second pulse wave signal, and authenticating the user based on the cross-correlation signal.

The authenticating the user includes, based on a peak value of the cross-correlation signal being equal to or greater than a first threshold value, authenticating the user.

The method further includes obtaining a deviation score between the denoised first pulse wave signal and the denoised second pulse wave signal by comparing a peak-to-peak interval between the denoised first pulse wave signal and the denoised second pulse wave signal, a pulse interval or a systolic peak, and authenticating the user based on the deviation score.

The authenticating the user includes, based on the deviation score being less than a second threshold value, authenticating the user.

The receiving includes transmitting time stamp information corresponding to the first pulse wave signal and a signal for requesting the second pulse wave signal to the wearable device and the second pulse wave signal may be obtained based on the time stamp information.

The method further includes identifying whether the user is in a sleeping state, and based on identifying that the user is in a sleeping state, maintaining a locked state of the electronic apparatus regardless of whether the user is authenticated.

The method further includes identifying a heart rate of the user, based on identifying that the heart rate of the user is equal to or less than a third threshold value or equal to or greater than a fourth threshold value, performing a face scan of the user using a camera of the electronic apparatus, identifying whether the user is conscious based on the face scan, and based on identifying that the user is unconscious, maintaining a locked state of the electronic apparatus regardless of whether the user is authenticated.

The method further includes, based on the user authentication being failed while the electronic apparatus is in an unlocked state, switching the electronic apparatus to a locked state.

The method further includes obtaining fingerprint information of the user through a fingerprint sensor included in the electronic apparatus, and the authenticating the user includes, based on the fingerprint information matching fingerprint information stored in the electronic apparatus and the peak value being equal to or greater than a first threshold value, authenticating the user.

The method further includes identifying a user by comparing the first pulse wave signal or the second pulse wave signal with a third pulse wave signal stored in the electronic apparatus.

In accordance with another aspect of the disclosure, an electronic apparatus is provided. The electronic apparatus includes a first pulse wave sensor, a communication interface, memory storing one or more computer programs, and one or more processors communicatively coupled to the first pulse wave sensor, the communication interface, and the memory, wherein the one or more computer programs include computer-executable instructions that, when executed by the one or more processors, cause the electronic apparatus to, based on a user touch for the first pulse wave sensor being detected, obtain a first pulse wave signal through the first pulse wave sensor and receive a second pulse wave signal detected through a second pulse wave sensor included in a wearable device from the wearable device, remove noise of the first pulse wave signal and the second pulse wave signal using a band pass filter, obtain a cross-correlation signal indicating a correlation between denoised first pulse wave signal and the denoised second pulse wave signal, and authenticate a user based on the cross-correlation signal.

The one or more computer programs further include computer-executable instructions that, when executed by the one or more processors, cause the electronic apparatus to, based on a peak value of the cross-correlation signal being equal to or greater than a first threshold value, authenticate the user.

The one or more computer programs further include computer-executable instructions that, when executed by the one or more processors, cause the electronic apparatus to obtain a deviation score between denoised first pulse wave signal and the denoised second pulse wave signal by comparing a peak-to-peak interval between the first pulse wave signal and the second pulse wave signal, a pulse interval or a systolic peak, and authenticate the user based on the deviation score.

The one or more computer programs further include computer-executable instructions that, when executed by the one or more processors, cause the electronic apparatus to, based on the deviation score being less than a second threshold value, authenticate the user.

The one or more computer programs further include computer-executable instructions that, when executed by the one or more processors, cause the electronic apparatus to transmit time stamp information corresponding to the first pulse wave signal and a signal for requesting the second pulse wave signal to the wearable device, and the second pulse wave signal may be obtained based on the time stamp information.

The one or more computer programs further include computer-executable instructions that, when executed by the one or more processors, cause the electronic apparatus to identify whether the user is in a sleeping state, and based on identifying that the user is in a sleeping state, maintain a locked state of the electronic apparatus regardless of whether the user is authenticated.

The one or more computer programs further include computer-executable instructions that, when executed by the one or more processors, cause the electronic apparatus to identify a heart rate of the user, based on identifying that the heart rate of the user is equal to or less than a third threshold value or equal to or greater than a fourth threshold value, perform a face scan of the user using a camera of the electronic apparatus, identify whether the user is conscious based on the face scan, and based on identifying that the user is unconscious, maintain a locked state of the electronic apparatus regardless of whether the user is authenticated.

The one or more computer programs further include computer-executable instructions that, when executed by the one or more processors, cause the electronic apparatus to, based on the user authentication being failed while the electronic apparatus is in an unlocked state, switch the electronic apparatus to a locked state.

The one or more computer programs further include computer-executable instructions that, when executed by the one or more processors, cause the electronic apparatus to obtain fingerprint information of the user through a fingerprint sensor included in the electronic apparatus, and based on the fingerprint information matching fingerprint information stored in the electronic apparatus and the peak value being equal to or greater than a first threshold value, authenticate the user.

In accordance with another aspect of the disclosure, one or more non-transitory computer readable recording media storing computer-executable instructions that, when executed by one or more processors of an electronic device, cause the electronic apparatus to perform operations are provided. The operations include based on a user touch for a first pulse wave sensor included in the electronic apparatus being detected, obtaining a first pulse wave signal through the first pulse wave sensor and receiving a second pulse wave signal detected through a second pulse wave sensor included in a wearable device from the wearable device, removing noise of the first pulse wave signal and the second pulse wave signal using a band pass filter, obtaining a cross-correlation signal indicating a correlation between denoised first pulse wave signal and the denoised second pulse wave signal, and authenticating a user based on the cross-correlation signal.

Through the above-described embodiments, by comparing a pulse wave signal obtained from a wearable device and a pulse wave signal obtained from an electronic apparatus, there is an effect of preventing the issue of a user authentication system being neutralized by an authenticated user operating the electronic apparatus and improving the security of the user authentication system.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1A:
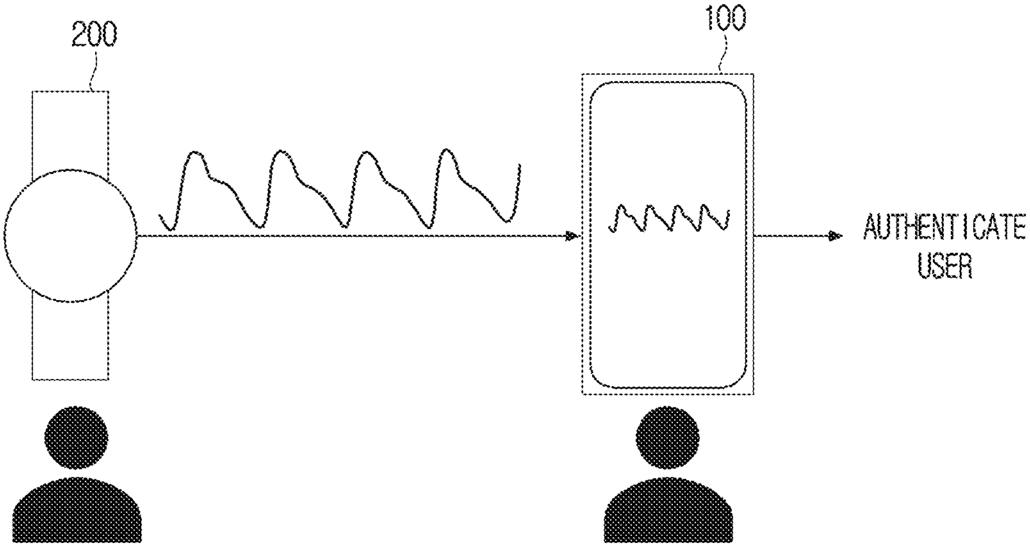
FIGS. 1A and 1B are views provided to describe a user authentication system according to various embodiments of the disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments, of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

In the disclosure, an expression "have," "may have," "include," "may include" or the like, indicates existence of a corresponding feature (for example, a numerical value, a function, an operation or a component, such as a part), and does not exclude existence of an additional feature.

In the disclosure, expressions "A or B," "least one of A and/or B," "one or more of A and/or B" and the like, may include all possible combinations of items enumerated together. For example, "A or B," "at least one of A and B" or "at least one of A or B" may indicate all of 1) a case where at least one A is included, 2) a case where at least one B is included, or 3) a case where both of at least one A and at least one B are included.

Expressions "first," "second" and the like, used in the disclosure may indicate various components regardless of a sequence or importance of the components. These expressions are used only to distinguish one component from another component, and do not limit the corresponding components.

In case that any component (for example, a first component) is mentioned to be "(operatively or communicatively) coupled with/to" or "connected to" another component (for example, a second component), it is to be understood that any component is directly coupled to another component or may be coupled to another component through still another component (for example, a third component).

On the other hand, in case that any component (for example, a first component) is mentioned as being "directly coupled" or "directly connected" to another component (for example, a second component), it is to be understood that still another component (for example, a third component) does not exist between any component and another component.

An expression "configured (or set) to" used in the disclosure may be replaced by an expression "suitable for," "having the capacity to," "designed to," "adapted to," "made to" or "capable of" based on a situation. The expression "configured (or set) to" may not necessarily indicate "specifically designed to" in hardware.

Instead, an expression a "device configured to" in any situation may indicate that the device may "perform~" together with another device or component. For example, "a processor configured (or set) to perform A, B and C" may indicate a dedicated processor (for example, an embedded processor) for performing the corresponding operations or a generic-purpose processor (for example, a central processing unit (CPU) or an application processor) that may perform the corresponding operations by executing one or more software programs stored in memory device.

In the embodiments, a "module" or a "~er/or" may perform at least one function or operation, and be implemented by hardware or software, or be implemented by a combination of hardware and software. In addition, a plurality of "modules" or a plurality of "~ers/ors" may be integrated in at least one module and implemented by at least one processor except for a "module" or an "~er/or" that needs to be implemented by specific hardware.

Meanwhile, various elements and regions in the drawings are schematically shown. Therefore, the spirit of the disclosure is not limited by relative sizes or intervals shown in the accompanying drawings.

It should be appreciated that the blocks in each flowchart and combinations of the flowcharts may be performed by one or more computer programs which include computer-executable instructions. The entirety of the one or more computer programs may be stored in a single memory device or the one or more computer programs may be divided with different portions stored in different multiple memory devices.

Any of the functions or operations described herein can be processed by one processor or a combination of processors. The one processor or the combination of processors is circuitry performing processing and includes circuitry like an application processor (AP, e.g., a central processing unit (CPU)), a communication processor (CP, e.g., a modem), a graphical processing unit (GPU), a neural processing unit (NPU) (e.g., an artificial intelligence (AI) chip), a wireless-fidelity (Wi-Fi) chip, a Bluetooth™ chip, a global positioning system (GPS) chip, a near field communication (NFC) chip, connectivity chips, a sensor controller, a touch controller, a finger-print sensor controller, a display drive integrated circuit (IC), an audio CODEC chip, a universal serial bus (USB) controller, a camera controller, an image processing IC, a microprocessor unit (MPU), a system on chip (SoC), an IC, or the like.

Hereinafter, the embodiments of the disclosure are described with reference to the accompanying drawings for those skilled in the art to which the disclosure pertains to easily practice the disclosure.

Figure 1B:
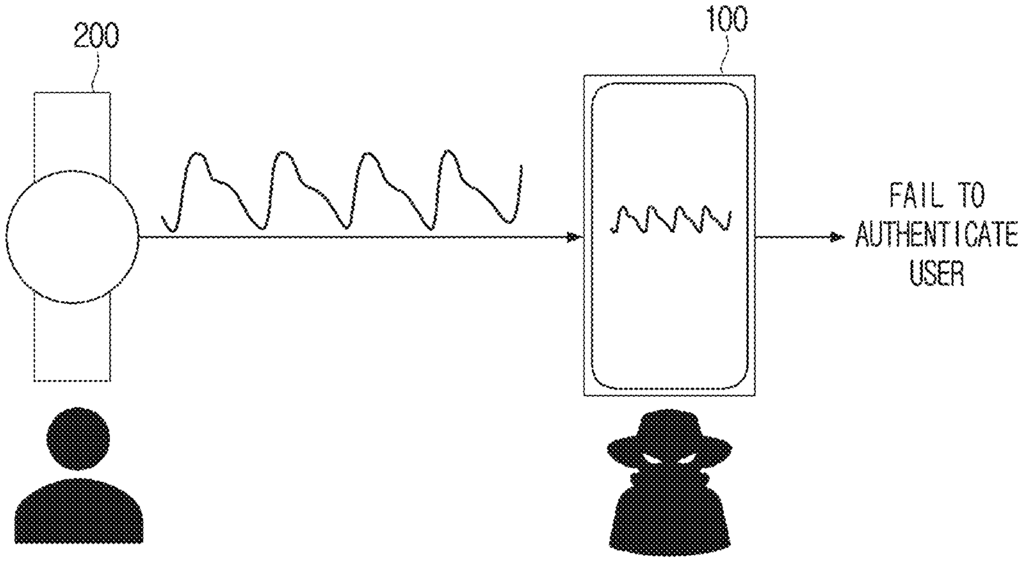

FIGS. 1A and 1B are views provided to describe a user authentication system according to various embodiments of the disclosure.

Referring to FIGS. 1A and 1B, when a user touch for a first pulse wave sensor included in an electronic apparatus 100 is detected, the electronic apparatus 100 may obtain a first pulse wave signal through the first pulse wave sensor, and a wearable device 200 may obtain a second pulse wave signal through a second pulse wave sensor.

In this case, the second pulse wave signal may be a pulse wave signal obtained based on time stamp information corresponding to the first pulse wave signal.

The electronic apparatus 100 may authenticate the user by comparing the first pulse wave signal and the second pulse wave signal.

For example, referring to FIG. 1A, when the electronic apparatus 100 identifies that the first pulse wave signal and the second pulse wave signal are obtained from the same user by comparing the first pulse wave signal and the second pulse wave signal, the electronic apparatus 100 may authenticate the user.

However, referring to FIG. 1B, when the electronic apparatus 100 identifies that the first pulse wave signal and the second pulse wave signal are obtained from different users by comparing the first pulse wave signal and the second pulse wave signal, the user authentication may fail.

Figure 2:
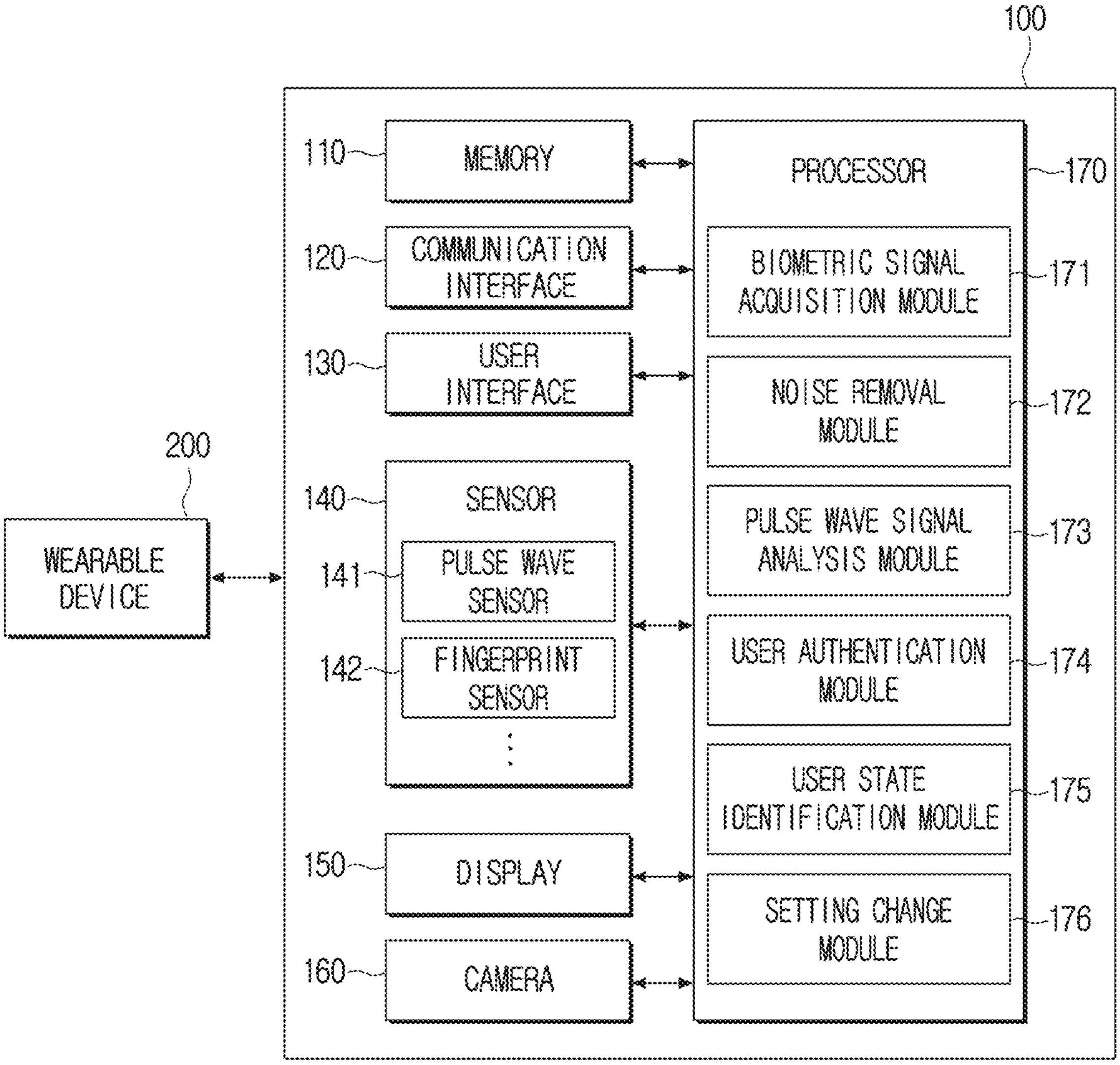
FIG. 2 is a block diagram provided to describe configuration of an electronic apparatus according to an embodiment of the disclosure.

FIG. 2 is a block diagram provided to describe the configuration of an electronic apparatus according to an embodiment of the disclosure.

Referring to FIG. 2, an electronic apparatus 100 may include memory 110, a communication interface 120, a user interface 130, a sensor 140, a display 150, and a processor 170. The electronic apparatus 100 may omit some of the above components, or may further include other components. The electronic apparatus 100 may be a smartphone, but this is only an example. The electronic apparatus 100 may be implemented through various devices.

The memory 110 may store at least one instruction regarding the electronic apparatus 100. The memory 110 may store an operating system (O/S) for driving the electronic apparatus 100. In addition, the memory 110 may store various software programs or applications for the electronic apparatus 100 to operate according to various embodiments. In addition, the memory 110 may store semiconductor memory, such as flash memory or a magnetic storage medium, such as a hard disk.

Specifically, the memory 110 may store various software modules for the electronic apparatus 100 to operate according to various embodiments, and the processor 170 may control the operation of the electronic apparatus 100 by executing the various software modules stored in the memory 110. In other words, the memory 110 may be accessed by the processor 170, and reading/recording/modifying/deleting/updating data by the processor 170 may be performed.

In addition, the memory 110 may store fingerprint information of the user for authenticating the user. Further, the memory 110 may store at least one algorithm for identifying the user's state (e.g., whether the user is in a sleeping state or whether the user is conscious) through the user's face image obtained through the camera 160.

Meanwhile, the term 'memory 110' herein may be meant to include the memory 110, read only memory (ROM) (not shown) or random access memory (RAM) (not shown) in the processor 170, or memory card (not shown) (e.g., a micro secure digital (SD) card or memory stick) mounted in the electronic apparatus 100.

The communication interface 120 may include circuitry and communicate with an external apparatus and a server. The communication interface 120 may perform communication with the external apparatus or the server based on a wired or wireless communication method. The communication interface 120 may include a wireless-fidelity (Wi-Fi) module (not shown), a Bluetooth module (not shown), an infrared (IR) module, a local area network (LAN) module, an Ethernet module, or the like. Here, each communication module may be implemented in the form of at least one hardware chip. In addition to the above-described communication methods, a wireless communication module may include at least one communication chip performing communication based on various wireless communication standards, such as Zigbee, universal serial bus (USB), mobile industry processor interface camera serial interface (MIPI CSI), third generation (3G), 3rd generation partnership project (3GPP), long term evolution (LTE), LTE advanced (LTE-A), 4th generation (4G), and 5th generation (5G). However, this configuration is only an example, and the communication interface 120 may use at least one communication module among various communication modules.

The user interface 130 is configured to receive a user command for controlling the electronic apparatus 100. The user interface 130 may be implemented as a device, such as a button, a touch pad, a mouse, or a keyboard, or may be implemented as a touch screen that may also perform a display function and a manipulation input function. Here, the button may be provided in various types, such as a mechanical button, a touch pad, a wheel, and the like, which are formed in arbitrary areas, such as a front portion, a side portion, or a back portion of an exterior of a main body of the electronic apparatus 100. The electronic apparatus 100 may obtain various user inputs through the user interface 130. The electronic apparatus 100 may identify that the user is in a sleeping state through a user input that is input through the user interface 130.

The sensor 140 may include a pulse wave sensor 141 and a fingerprint sensor 142, but is not limited thereto. The sensor 140 may include a sensor for obtaining the user's various biometric signals. For example, the sensor 140 may include a motion sensor (not shown), and the motion sensor may detect the user's movement.

The pulse wave sensor 141 is a sensor for sensing the user's pulse wave signal, and may be a photoplethysmography (PPG) sensor. Here, the pulse wave signal may be a photoplethysmography (PPG) signal.

A pulse wave is a pulsating waveform that appears as blood waves in the heart, and there may be changes in blood flow and subsequent changes in blood vessel volume due to the relaxation and contraction of the heart. Each time the heart beats, blood vessels expand due to pressure pulses and thus, the arterial blood flow varies, resulting in changes in light transmittance or reflectance. Here, based on the changes in light transmittance and reflectance, the pulse wave sensor 141 may detect a pulse wave signal.

Specifically, the pulse wave sensor 141 may obtain a pulse wave signal by sensing an optical signal in time series through an optical sensor that receives the light irradiated from a light source and then scattered or reflected from the user's blood vessels and herein, the optical sensor may be implemented as a photo diode, a photo transistor, an image sensor, or the like.

The electronic apparatus 100 may authenticate the user by comparing the user's first pulse wave signal obtained through the pulse wave sensor 141 and the second pulse wave signal detected through sensing from the pulse wave sensor included in the wearable device 200.

The fingerprint sensor 142 may obtain the user's fingerprint information. The fingerprint information obtained through the fingerprint sensor 142 is stored as image information, and after being compared with the user's fingerprint information pre-stored in the memory 110, may be used to authenticate the user of the electronic apparatus 100 according to a match score (e.g., matching rate or similarity). The fingerprint information obtained through the fingerprint sensor 420 may be compressed and stored, and may be stored in the memory 110 as the user's authentication information for future user authentication. The fingerprint information extracted through the fingerprint sensor 420 may be stored in the memory 110 as a feature template.

Figure 3:
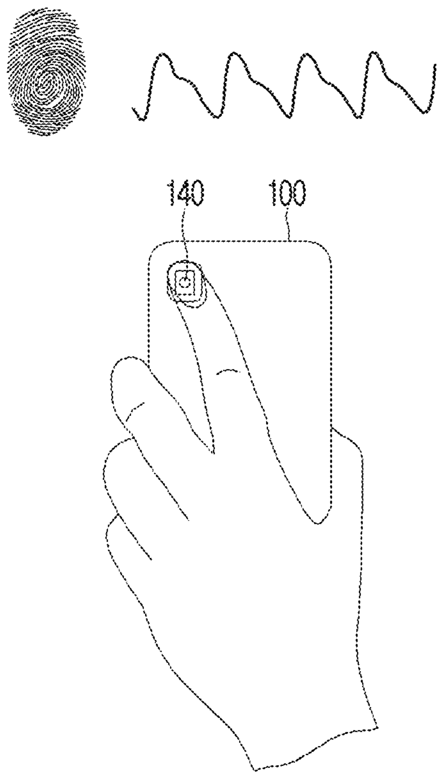
FIG. 3 is a view provided to describe a method for obtaining a pulse wave signal and fingerprint information according to an embodiment of the disclosure.

FIG. 3 is a view provided to describe a method for obtaining a pulse wave signal and fingerprint information according to an embodiment of the disclosure.

Referring to FIG. 3, the pulse wave sensor 141 or the fingerprint sensor 142 may be placed on the back of the electronic apparatus 100 as illustrated in FIG. 3, but is not limited thereto. The pulse wave sensor 141 or the fingerprint sensor 142 may be placed to cover at least some areas or the entire areas of the display 150. The pulse wave sensor 141 or the fingerprint sensor 142 may obtain the user's pulse wave signal or fingerprint information at the same time when the user applies a touch input to the pulse wave sensor 141 or the fingerprint sensor 142.

Hereinafter, the description will be focused on the embodiments of sensing the pulse wave signal or fingerprint information of a user (or a subject being measured) and authenticating the user, but the technical idea of the disclosure is not limited thereto. The technical idea of the disclosure may be applied when sensing various biometric signals (e.g., an electrocardiogramaignal, an electromyography (EMG) signal) or receiving them from the wearable device 200 and using them to authenticate a user.

The display 150 may be implemented as a display including a self-light emitting element or a display including a non-light emitting element and a backlight. For example, the display may be implemented in various types of displays, such as a liquid crystal display (LCD), an organic light emitting diodes (OLED) display, a light emitting diodes (LED), a micro light emitting diode (micro LED), a mini LED, a plasma display panel (PDP), a quantum dot (QD) display, a quantum dot light-emitting diode (QLED). The display 150 may also include a driving circuit, a backlight unit, and the like, which may be implemented in a form, such as an a-si thin film transistor (TFT), a low temperature poly silicon (LTPS) TFT, an organic TFT (OTFT), or the like. In particular, the display 150 may display an image obtained through a camera 160.

The camera 160 is configured to photograph a subject to generate a captured image. Here, the captured image may include both a moving image and a still image. The camera 160 may obtain an image of the exterior of the electronic apparatus 100, and may be implemented as a lens, an infrared sensor, or the like.

More particularly, the camera 160 may be arranged to captures images of the front or rear direction of the electronic apparatus 100, and may generate an image by capturing a user present at the front or rear of the electronic apparatus 100. In particular, the camera 160 may scan the user's face.

The processor 170 may control the overall operations and functions of the electronic apparatus 100. Specifically, the processor 170 is connected to the configuration of the electronic apparatus 100 including the memory 110, and as described above, by executing at least one instruction stored in the memory 110, may control the overall operations of the electronic apparatus 100.

The processor 170 may be implemented in various ways. For example, the processor 170 may be implemented as at least one of an application specific integrated circuit (ASIC), an embedded processor, a microprocessor, hardware control logic, a hardware finite state machine (FSM), or a digital signal processor (DSP). Meanwhile, the term 'processor 170' in the disclosure may be meant to include a central processing unit (CPU), a graphic processing unit (GPU), a main processing unit (MPU), or the like.

The processor 170 may include a biometric signal acquisition module 171, a noise removal module 172, a biometric signal analysis module 173, a user authentication module 174, a user state identification module 175, and a setting change module 176. A plurality of modules according to an embodiment may be implemented as software modules or hardware modules, and when the plurality of modules are implemented as software modules, the processor 170 may access the software modules by loading the software modules stored in the memory 110.

When the user's touch for the pulse wave sensor 141 included in the electronic apparatus 100 is detected, the biometric signal acquisition module 171 may obtain a first pulse wave signal through the pulse wave sensor 141 and receive a second pulse wave signal detected through a pulse wave sensor included in the wearable device 200 from the wearable device 200.

The biometric signal acquisition module 171 may transmit time stamp information corresponding to the first pulse wave signal, measurement time, and a signal for requesting the second pulse wave signal to the wearable device 200. Here, the time stamp information may be time stamp information regarding the time when the user's touch is detected through the pulse wave sensor 141, the time when the user's touch is detected, the time after a predetermined time from the time when the user's touch is detected, or the time when the first pulse wave signal begins to be obtained through the pulse wave sensor 141.

The measurement time may be a value that is pre-stored in the memory 110, but is not limited thereto. The measurement time may be a value input through the user interface 130, the time when the user's touch is detected through the pulse wave sensor 141 or the time when a pulse wave signal is measured through the pulse wave sensor 141.

The second pulse wave signal may be obtained based on the time stamp information and the measurement time.

For example, when the time stamp information corresponding to the first pulse wave signal is 'Mon Nov. 8, 2021 10:00' and the measurement time is '10 seconds', the second pulse wave signal may be a pulse wave signal measured for 10 seconds from 10 O'clock, Monday, Nov. 8, 2021.

The wearable device 200 may obtain the second pulse wave signal and transmit it to the electronic apparatus 100 based on the received time stamp information and measurement time, but is not limited thereto. The wearable device 200 may transmit the second pulse wave signal corresponding to the time stamp information and measurement time received from the electronic apparatus 100 from among pre-obtained pulse wave signals, to thee electronic apparatus 100.

When the user's touch for the fingerprint sensor 142 included in the electronic apparatus 100 is detected, the biometric signal acquisition module 171 may obtain the user's fingerprint information through the fingerprint sensor 142.

The noise removal module 172 may remove noise included in a pulse wave signal using a filter. Specifically, the noise removal module 172 may remove noise of the first pulse wave signal and the second pulse wave signal using a band pass filter. For example, when the pulse wave signal is a signal sampled at a sampling rate of 10 Hz, the frequency band of the pulse wave signal may be 0 to 5 Hz. In this case, assuming that a person's heart rate is 60 BPM (1 Hz) to 150 BPM (2.5 Hz), frequency bands other than 1 Hz to 2.5 Hz may be noise frequency bands. Based on a band pass filter that passes signals with a frequency of 1 Hz to 2.5 Hz, the noise removal module 172 may obtain the first pulse wave signal and the second pulse wave signal.

The biometric signal analysis module 173 may compare the first pulse wave signal and the second pulse wave signal to identify whether the user of the electronic apparatus 100 (i.e., the user corresponding to the first pulse wave signal) and the user of the wearable device 200 (i.e., the user corresponding to the second pulse wave signal) are identified as the same user. When the user of the electronic apparatus 100 and the user of the wearable device 200 are identified as the same user, the user authentication module 174 may authenticate the user.

Figure 4:
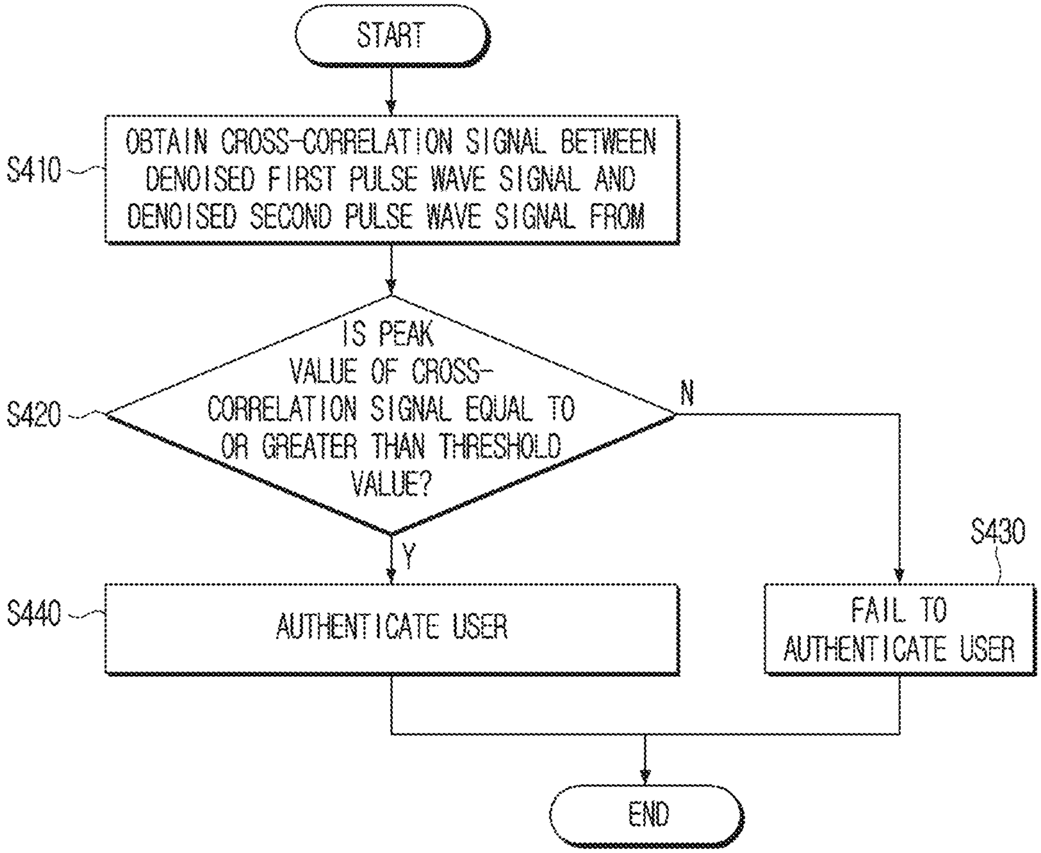
FIG. 4 is a view provided to describe a method of performing user authentication using a cross-correlation signal of a first pulse wave signal and a second pulse wave signal according to an embodiment of the disclosure.

FIG. 4 is a view provided to describe a method of performing user authentication using a cross-correlation signal of a first pulse wave signal and a second pulse wave signal according to an embodiment of the disclosure.

Referring to FIG. 4, the biometric signal analysis module 173 may obtain a cross correlation signal indicating a correlation between the first pulse wave signal and the second pulse wave signal at operation S410. Here, the obtained cross correlation signal may be as shown in FIGS. 5A and 5B.

Figure 5A:
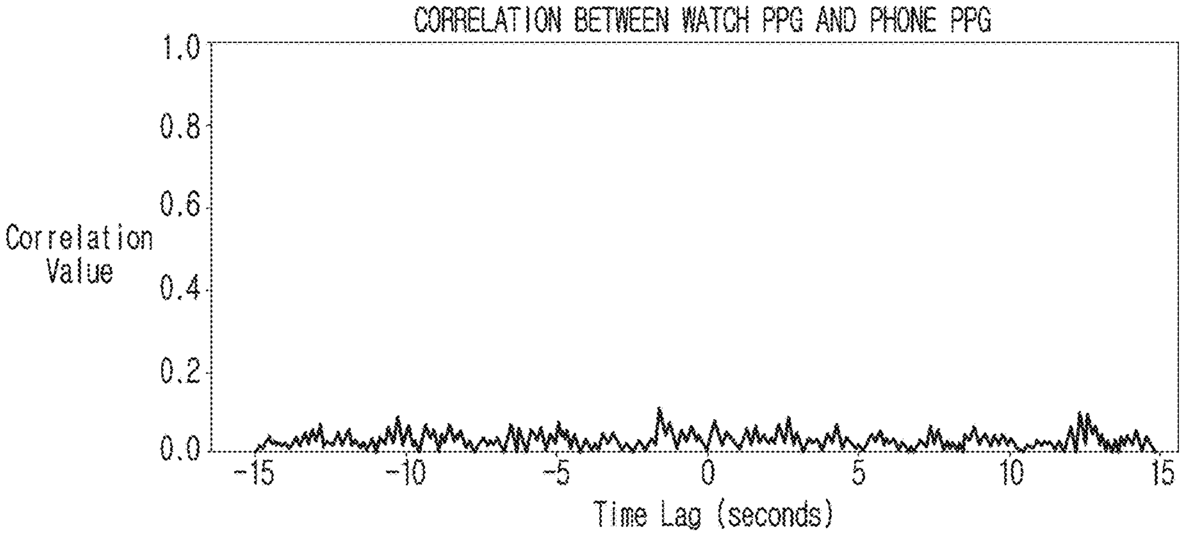
FIGS. 5A and 5B are views provided to describe a method of performing user authentication using a cross-correlation signal of a first pulse wave signal and a second pulse wave signal according to various embodiments of the disclosure.
Figure 5B:
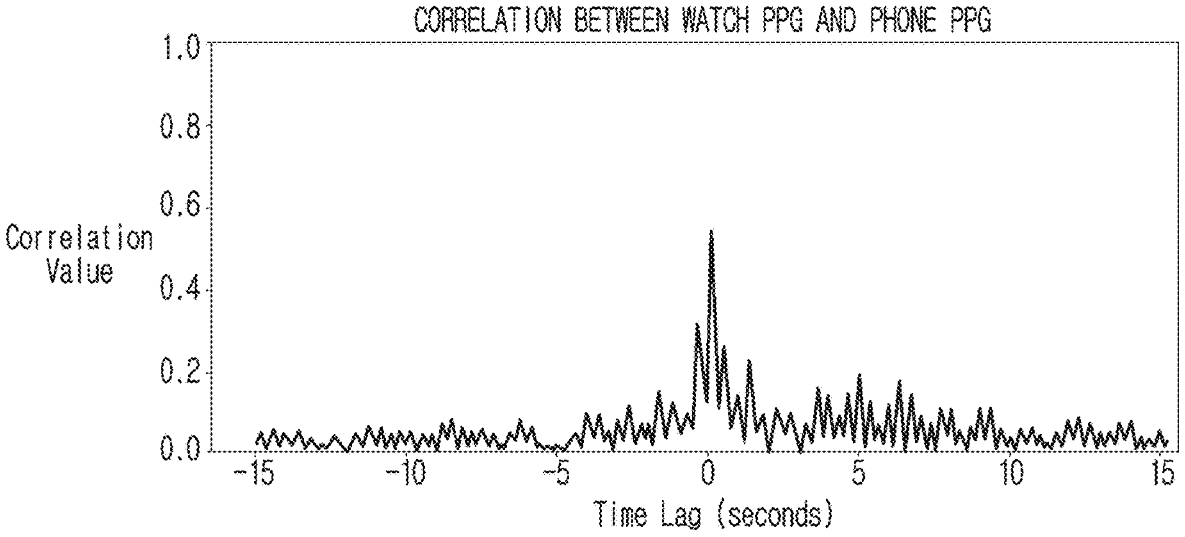

FIGS. 5A and 5B are views provided to describe a method of performing user authentication using a cross-correlation signal of a first pulse wave signal and a second pulse wave signal according to various embodiments of the disclosure.

Referring to FIGS. 5A and 5B, meanwhile, hereinafter, the description will focus on the embodiments of removing noise of the first pulse wave signal and the second pulse wave signal, comparing the first pulse wave signal and the second pulse wave signal and authenticating the user, but the technical idea of the disclosure is not limited thereto. The technical idea of the disclosure may be applied when authenticating the user by comparing the first pulse wave signal and the second pulse wave signal without removing noise or skipping the step of removing noise in one of the first pulse wave signal and the second pulse wave signal.

The cross correlation signal is a signal for obtaining a correlation (or degree of correlation, correlation, similarity) between two signals. Here, the cross correlation signal may be obtained by a cross correlation function as shown in Equation 1 below.

$$S3(\tau) = \int_{-\infty}^{\infty} S1(t)S2(t+\tau)d\tau \qquad \text{Equation 1}$$

In Equation 1, S1 may represent the first pulse wave signal, S2 may represent the second pulse wave signal, and S3 may represent a cross correlation signal.

The biometric signal analysis module 173 may obtain the correlation between the first pulse wave signal and the second pulse wave signal through the signal characteristics of the obtained cross correlation signal. Here, the correlation between the first pulse wave signal and the second pulse wave signal may correspond to at least one peak value of the cross correlation signal. Specifically, the biometric signal analysis module 173 may identify at least one peak value from the obtained cross correlation signal. For example, the biometric signal analysis module 173 may identify the peak value with the largest absolute value from among peak values in the cross correlation signal. Alternatively, the biometric signal analysis module 173 may identify the peak value at the point where the time lag is 0 or the peak value at the point closest to the point where the time lag is 0 in the cross correlation signal. Here, the higher the degree of correlation between the first pulse wave signal and the second pulse wave signal (i.e., the higher the similarity), the greater the absolute value of the peak value identified in the cross correlation signal.

The user authentication module 174 may authenticate the user based on the cross correlation signal (or signal characteristics of the cross correlation signal). Specifically, the user authentication module 174 may identify whether the peak value of the cross correlation signal is equal to or greater than a first threshold value at operation S420. Here, when the peak value of the cross correlation signal is less than the first threshold value at operation S420-N, the user authentication module 174 may identify that user authentication has failed at operation S430. When the peak value of the cross correlation signal is equal to or greater than the first threshold value at operation S420-Y, the user authentication module 174 may authenticate the user at operation S440.

For example, when the threshold value is 0.5, user authentication may fail when the cross correlation signal is obtained as illustrated in FIG. 5A, and user authentication may succeed when the cross correlation signal is obtained as illustrated in FIG. 5B.

Meanwhile, according to the above description, the user authentication module 174 authenticates the user based on the peak value of the cross correlation signal obtained by the biometric signal analysis module 173, but this is only an example. According to another embodiment, the user authentication module 174 may authenticate the user based on the deviation score between the first pulse wave signal and the second pulse wave signal, which is obtained by the biometric signal analysis module 173.

Figure 6:
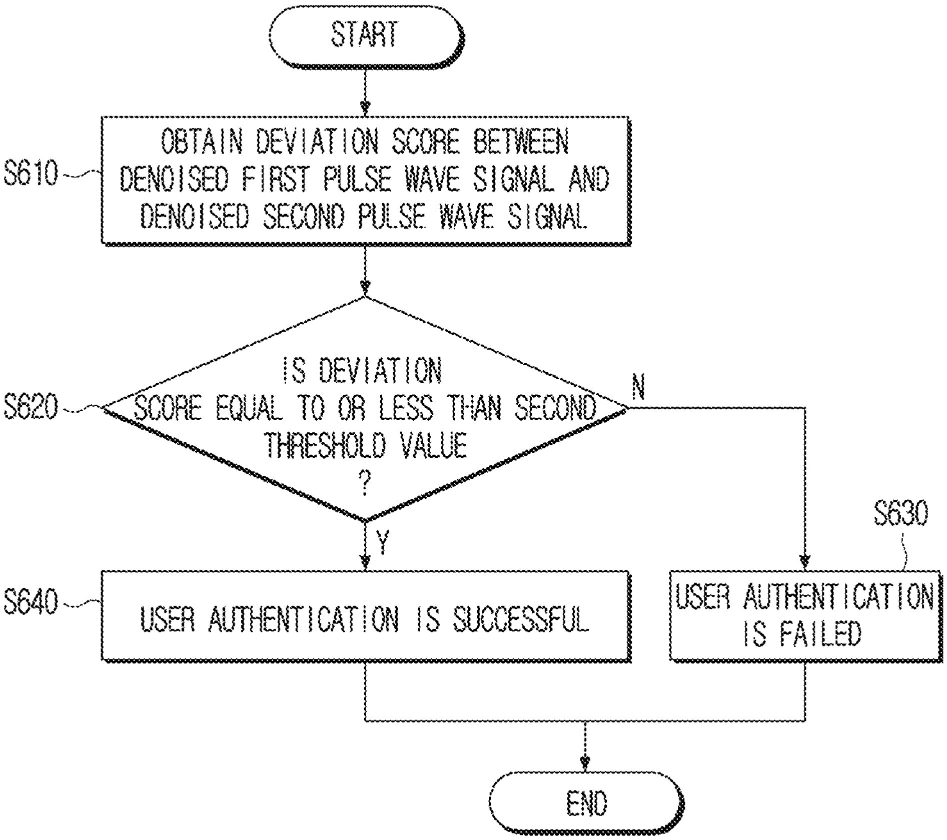
FIG. 6 is a view provided to describe a method of performing user authentication using a deviation score between a first pulse wave signal and a second pulse wave signal according to an embodiment of the disclosure.

FIG. 6 is a view provided to describe a method of performing user authentication using a deviation score between a first pulse wave signal and a second pulse wave signal according to an embodiment of the disclosure.

Referring to FIG. 6, the biometric signal analysis module 173 may obtain the deviation score between the first pulse wave signal and the second pulse wave signal by comparing a peak-to-peak interval (PPI) between the first pulse the first pulse wave signal and the second pulse wave signal, a pulse interval (PI) or a systolic peak (SP) at operation S610.

Figure 7:
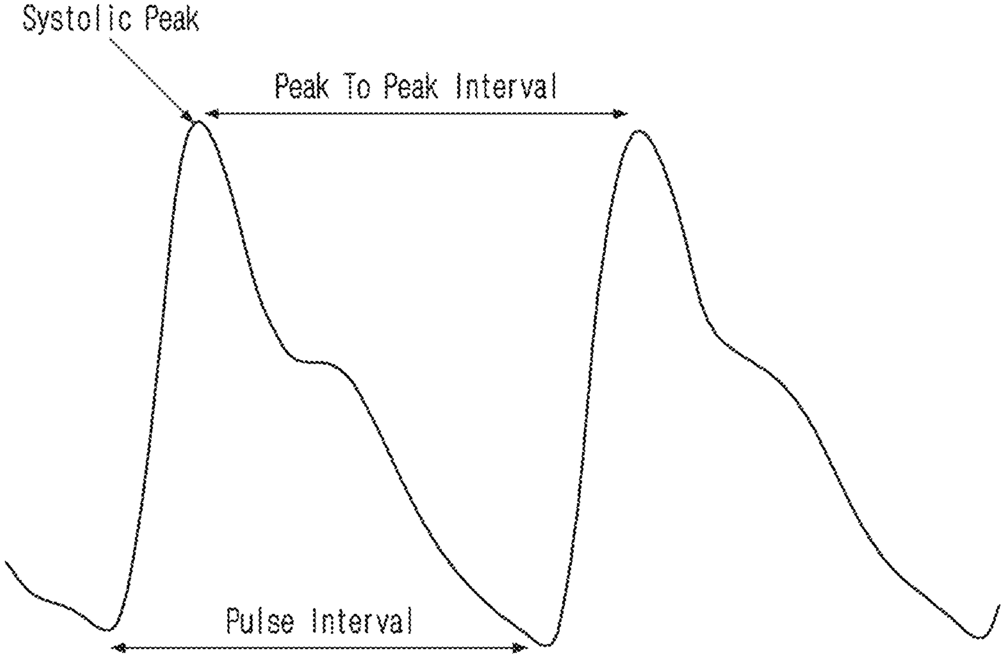
FIG. 7 is a view provided to describe a method of performing user authentication using a deviation score between a first pulse wave signal and a second pulse wave signal according to an embodiment of the disclosure.

FIG. 7 is a view provided to describe a method of performing user authentication using a deviation score between a first pulse wave signal and a second pulse wave signal according to an embodiment of the disclosure.

Referring to FIG. 7, the peak-to-peak interval (PPI), the pulse interval (PI) or the systolic peak (SP) can be obtained, and the systolic peak may mean the point where the pulse wave value is the highest.

The biometric signal analysis module 173 may obtain the deviation score by Equation 2 below.

$$Dev(PPI) = \left|((PPI, 100) - (PPI, 200))/(PPI, 100)\right| \quad \text{Equation 2}$$

$$Dev(PPI) = \left|((PI, 100) - (PI, 200))/(PI, 100)\right|$$

$$Dev(PPI) = \left|((SP, 100) - (SP, 200))/(SP, 100)\right|$$

Dev(PPI), Dev(PI) and Dev(SP) may mean the deviation score according to the interval between the first pulse wave signal and the second pulse wave signal, the deviation score according to the pulse period and the deviation score according to the systole, respectively. (PPI, 100), (PPI, 200), (PI, 100), (PI, 200), (SP, 100), and (SP, 200) may mean the peak-to-peak interval of the electronic apparatus 100, the peak-to-peak interval of the wearable device 200, the pulse period of the electronic apparatus 100, the pulse period of the wearable device 200, the systolic peak of the electronic apparatus 100, and the systolic peak of the wearable device 200, respectively.

Here, the deviation score may mean one of Dev(PPI), Dev(PI) and Dev(SP), but is not limited thereto. The deviation score may be obtained in various ways, such as the weighted average value of Dev(PPI), Dev(PI) and Dev(SP) using Equation 3 below.

$$\text{Deviation Score} = a * Dev(PPI) + b * Dev(PI) + c * Dev(SP) \quad \text{Equation 3}$$

Here, a, b and c may be arbitrary real numbers.

The user authentication module 174 may identify whether the deviation score is equal to or less than a second threshold value at operation S620.

When the deviation score exceeds the second threshold value, the user authentication module 174 may identify that user authentication has failed at operation S630.

When the deviation score is equal to or less than the second threshold value, the user authentication module 174 may authenticate the user at operation S640.

Meanwhile, the user authentication module 174 may identify the user based on the first pulse wave signal and the second pulse wave signal. Specifically, the memory 110 may store identification information (or identity information) of a registered user and information regarding a third pulse wave signal, and the user authentication module 174 may identify whether the user of the electronic apparatus 100 or the wearable device 200 is a registered user by comparing the first pulse wave signal (or the first pulse wave signal) or the second pulse wave signal (or the second pulse wave signal) and the third pulse wave signal. When it is identified that the user is a registered user, the user authentication module 174 may obtain the user's identification information (identity information).

Here, the method of comparing the first pulse wave signal or the second pulse wave signal and the third pulse wave signal may be the same as the method of comparing the first pulse wave signal and the second pulse wave signal. Meanwhile, as described above, the user authentication module 174 may identify the user based on a pulse wave signal, but is not limited thereto. Specifically, the memory 110 may store identification information of a registered user and various biometric signal information (e.g., fingerprint information), and the user authentication module 174 may identify the user of the electronic apparatus 100 or the wearable device 200 by comparing biometric signal information obtained through the electronic apparatus 100 or the wearable device 200 and the biometric signal information stored in the memory 110 and identify whether the identified user is a registered user.

Even if the user of the electronic apparatus 100 and the user of the wearable device 200 are identified as the same user, when the identified user is identified as not a registered user, user authentication may fail. When the identified user is identified as a registered user, the user authentication module 174 may authenticate the user. Accordingly, even if the user of the electronic apparatus 100 and the user of the wearable device 200 are identified as the same user by comparing the first pulse wave signal and the second pulse wave signal, by additionally identifying whether the user is the same user of the electronic apparatus 100, the security of the user authentication step can be further strengthened.

Meanwhile, it has been described above that the user authentication module 174 authenticates the user based on the user's pulse wave signal obtained through the pulse wave sensor 141, but the disclosure is not limited thereto. The user authentication module 174 may authenticate the user by additionally using the user's fingerprint information obtained through the fingerprint sensor 142.

Specifically, the user authentication module 174 may obtain the user's fingerprint information through the fingerprint sensor 142. When the user's fingerprint information obtained through the fingerprint sensor 142 and the fingerprint information stored in the memory 110 are the same and the peak value is equal to or greater than the first threshold value or the deviation score is equal to or less than the second threshold value, the user authentication module 174 may authenticate the user. Through the above-described method, the user authentication module 174 may authenticate the user in a method with more enhanced security.

When the user is authenticated, the setting change module 176 may change the setting state of the electronic apparatus 100.

For example, when the user is authenticated while the electronic apparatus 100 is in a locked state, the setting change module 176 may release the locked state of the electronic apparatus 100.

Alternatively, when the user is authenticated while the electronic apparatus 100 is in a child lock state, the setting change module 176 may release the child lock state of the electronic apparatus 100.

Alternatively, when the user is authenticated while a specific folder stored in the memory 110 is in a locked state, the setting change module 176 may allow the user to release the locked state of the specific folder and access the specific folder.

In addition, the setting change module 176 may change the setting state of the electronic apparatus 100 based on the user's identification information. In other words, the setting change module 176 may change the setting state differently depending on the identification information of the authenticated user.

For example, when a first user is authenticated while the electronic apparatus 100 is in a locked state and a child lock state, the setting change module 176 may release the locked state and the child lock state, but when a second user is authenticated while the electronic apparatus 100 is in a locked state and a child lock state, the setting change module 176 may release only the locked state and maintain the child lock state.

Meanwhile, the setting change module 176 may change the setting state of the electronic apparatus 100 based on the user's state.

The user state identification module 175 may identify the user's state. Here, the user may be the user of the electronic apparatus 100 or the user of the wearable device 200. The user's state may mean whether the user is in a sleeping state or whether the user is conscious.

When the user state identification module 175 identifies that the user is in a sleeping state or the user is unconscious, the setting change module 176 may maintain the setting state of the electronic apparatus 100 regardless of whether the user is authenticated.

Figure 8:
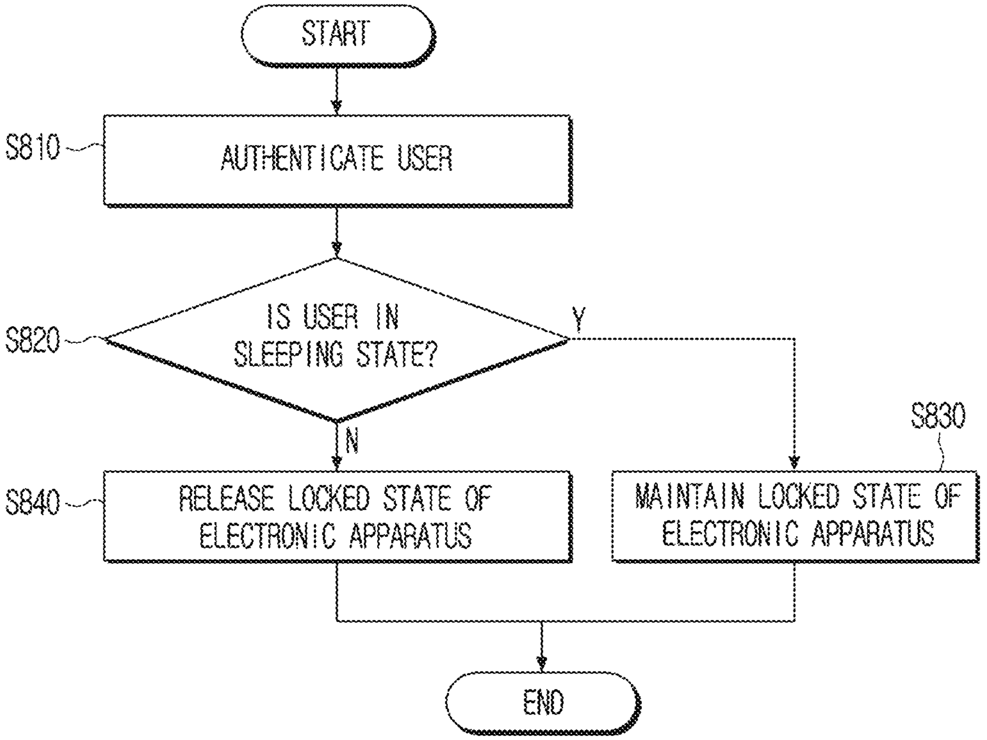
FIG. 8 is a view provided to describe a method of controlling an electronic apparatus according to whether a user is in a sleeping stat according to an embodiment of the disclosure.

FIG. 8 is a view provided to describe a method of controlling an electronic apparatus according to whether a user is in a sleeping stat according to an embodiment of the disclosure.

Referring to FIG. 8, the user authentication module 174 may authenticate the user at operation S810, and the user state identification module 175 may identify whether the user is in a sleeping state at operation S820. Specifically, it is possible to identify the user's heart rate based on the first pulse wave signal or the second pulse wave signal, and identify whether the user is in a sleeping state based on the identified heart rate. Alternatively, the user state identification module 175 may obtain information regarding whether the user is in a sleeping state through the wearable device 200, or identify that the user is in a sleeping state according to a user input that is input through the user interface 130.

When it is identified that the user is in a sleeping state at operation S820-Y, the setting change module 176 may maintain the locked state of the electronic apparatus 100 regardless of whether the user is authenticated at operation S830. When it is identified that the user is not in a sleeping state at operation S820-N, the setting change module 176 may release the locked state of the electronic apparatus 100.

Figure 9:
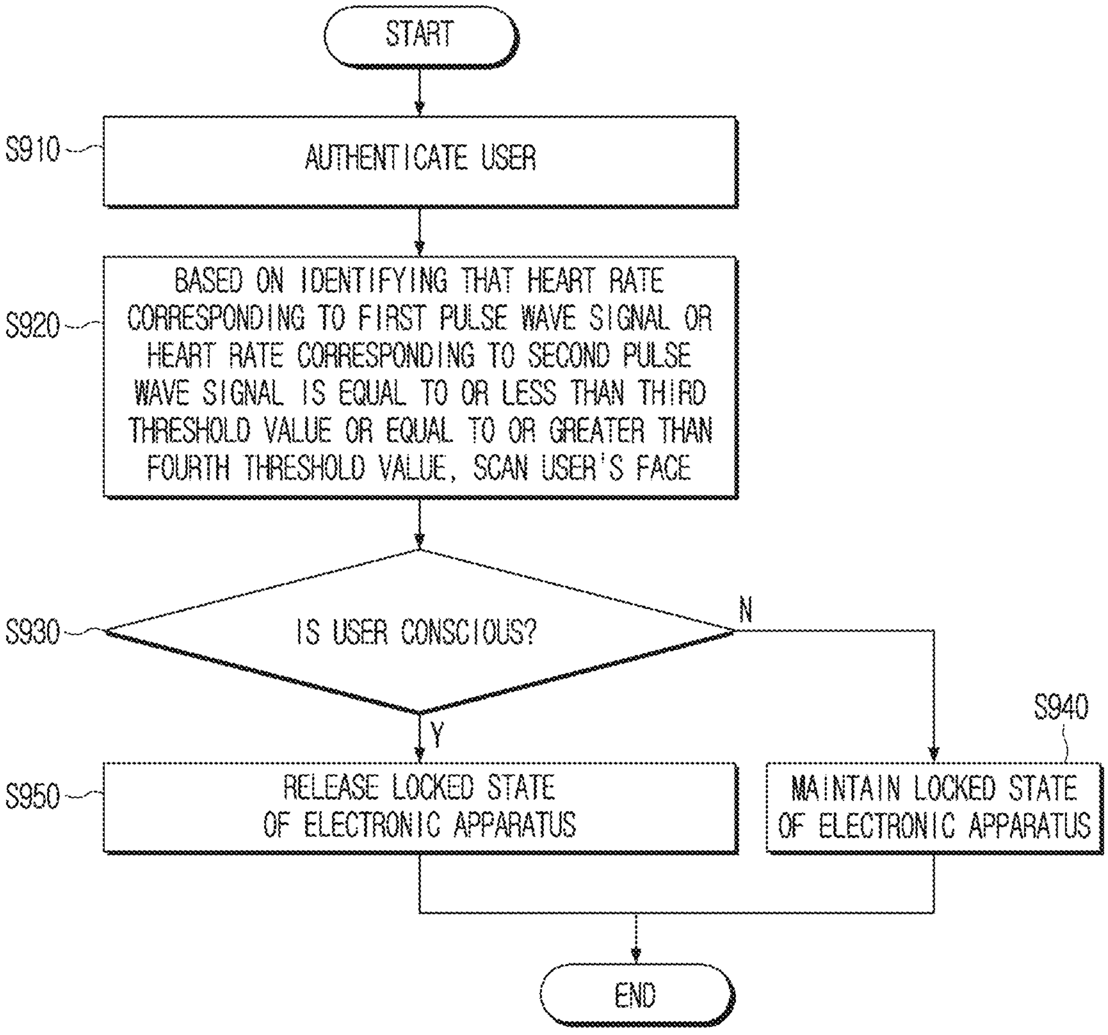
FIG. 9 is a view provided to describe a method of controlling an electronic apparatus according to whether a user is conscious according to an embodiment of the disclosure.

FIG. 9 is a view provided to describe a method of controlling an electronic apparatus according to whether a user is conscious according to an embodiment of the disclosure.

Referring to FIG. 9, the user authentication module 174 may authenticate the user at operation S910, and when the heart rate corresponding to the first pulse wave signal or the heart rate corresponding to the second pulse wave signal is equal to or less than a third threshold value or equal to or greater than a fourth threshold value, the user state identification module 175 may scan the user's face through the camera 160 at operation S920.

The user state identification module 175 may identify whether the user is conscious based on the face scan result at operation S930. Here, the user state identification module 175 may identify whether the user is conscious based on the user face scan result using an artificial intelligence technology using machine learning, such as deep learning and element technologies utilizing machine learning.

When it is identified that the user is unconscious at operation S930-N, the setting change module 176 may maintain the locked state of the electronic apparatus 100. When it is identified that the user is conscious at operation S940-Y, the locked state of the electronic apparatus 100 may be released at operation S950.

Meanwhile, it has been described that whether to release the locked state of the electronic apparatus varies depending on the user's state, but this is only an example. When it is identified that the user is in a sleeping state or unconscious, the setting change module 176 may maintain the setting state of the electronic apparatus 100, such as maintaining the locked state of a specific folder stored in the memory 110 regardless of whether the user is authenticated.

In addition, it has been described that the user is authenticated and the user's state is identified, but this is only an example. The user state identification module 175 may identify the user's state regardless of whether the user is authenticated.

Figure 10:
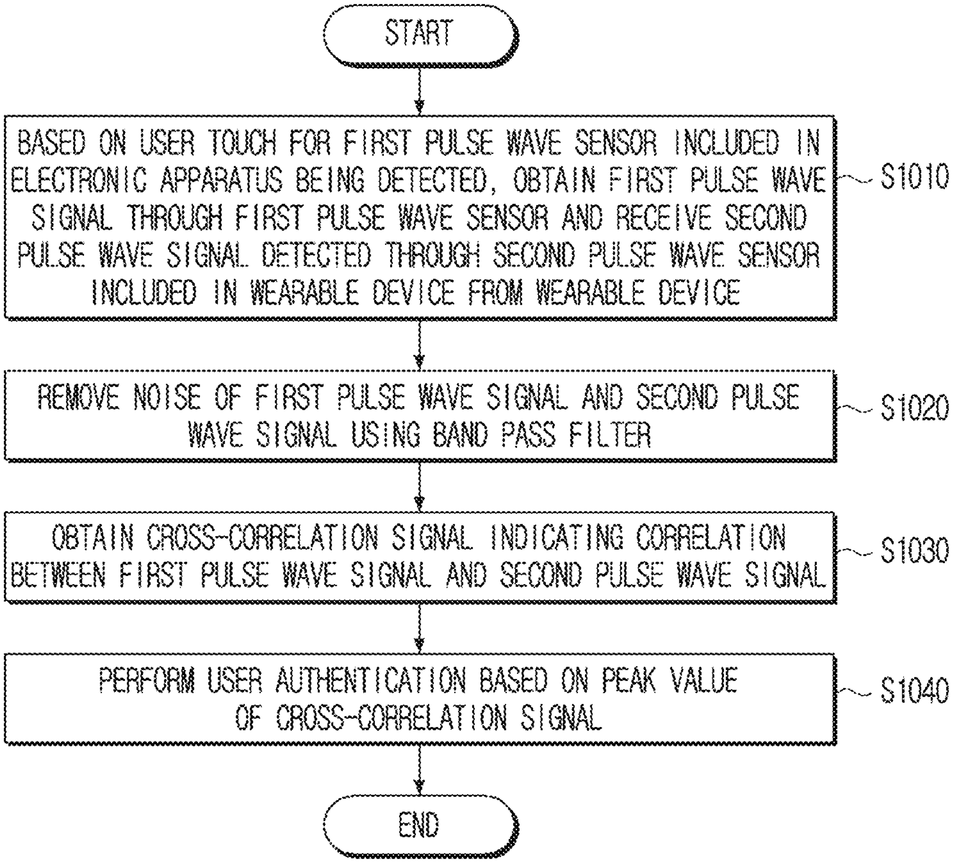
FIG. 10 is a view provided to describe a method of performing user authentication of an electronic apparatus according to an embodiment of the disclosure.

FIG. 10 is a view provided to describe a method of performing user authentication of an electronic apparatus according to an embodiment of the disclosure.

Referring to FIG. 10, when the user's touch for the first pulse wave sensor included in the electronic apparatus 100 is detected, the electronic apparatus 100 may obtain the first pulse wave signal through the first pulse wave sensor 141 and receive the second pulse wave signal detected through the second pulse wave sensor included in the wearable device 200 from the wearable device 200 at operation S1010.

The electronic apparatus 100 may remove noise of the first pulse wave signal and the second pulse wave signal using a band pass filter at operation S1020.

The electronic apparatus 100 may obtain a cross correlation signal indicating a correlation between the first pulse wave signal and the second pulse wave signal at operation S1030. Alternatively, the electronic apparatus 100 may obtain a deviation score between the first pulse wave signal and the second pulse wave signal.

The electronic apparatus 100 may perform user authentication based on the cross correlation signal at operation S1040. When the peak value of the cross correlation signal is equal to or less than the first threshold value, the electronic apparatus 100 may authenticate the user. Alternatively, when the deviation score is less than the second threshold value, the electronic apparatus 100 may authenticate the user. When the user is authenticated, the electronic apparatus 100 may change the setting state of the electronic apparatus 100.

Meanwhile, the term "part" or "module" used in the disclosure may include a unit consisting of hardware, software, or firmware, and may be interchangeably used with, for example, terms, such as a logic, a logical block, a component, or a circuit. In addition, "a part" or "a module" may be a component constituted as an integrated body or a minimum unit or a part thereof performing one or more functions. For example, a module may be constituted as an application-specific integrated circuit (ASIC).

In addition, the various embodiments of the disclosure may be implemented as software including instructions stored in machine-readable storage media, which can be read by machines (e.g., computers). The machines refer to devices that call instructions stored in a storage medium, and can operate according to the called instructions, and the devices may include an electronic device according to the aforementioned embodiments (e.g., electronic apparatus 100). In case an instruction is executed by a processor, the processor may perform a function corresponding to the instruction by itself, or by using other components under its control. An instruction may include a code that is generated or executed by a compiler or an interpreter. The machine-readable storage medium may be provided in a form of a non-transitory storage medium. Here, the term "non-transitory" means that the storage medium is tangible without including a signal, and does not distinguish whether data are semi-permanently or temporarily stored in the storage medium.

In addition, according to an embodiment of the disclosure, the above-described methods according to the diverse embodiments may be included and provided in a computer program product. The computer program product may be traded as a product between a seller and a purchaser. The computer program product may be distributed in a form of a storage medium (for example, compact disc read only memory (CD-ROM)) that may be read by the machine or online through an application store (for example, Play-Store™). In case of the online distribution, at least a portion of the computer program product may be at least temporarily stored in a storage medium, such as memory of a server of a manufacturer, a server of an application store, or a relay server or be temporarily generated.

Each of components (for example, modules or programs) according to various embodiments described above may include a single entity or a plurality of entities, and some of the corresponding sub-components described above may be omitted or other sub-components may be further included in the diverse embodiments. Alternatively or additionally, some components (for example, a module or a program) may be integrated into a single entity to perform the same or similar functions performed by each corresponding components prior to the integration. Operations performed by the modules, the programs, or the other components according to various embodiments may be executed in a sequential manner, a parallel manner, an iterative manner, or a heuristic manner, at least some of the operations may be performed in a different order or be omitted, or other operations may be added.

It will be appreciated that various embodiments of the disclosure according to the claims and description in the specification can be realized in the form of hardware, software or a combination of hardware and software.

Any such software may be stored in non-transitory computer readable storage media. The non-transitory computer readable storage media store one or more computer programs (software modules), the one or more computer programs include computer-executable instructions that, when executed by one or more processors of an electronic device, cause the electronic device to perform a method of the disclosure.

Any such software may be stored in the form of volatile or non-volatile storage such as, for example, a storage device like read only memory (ROM), whether erasable or rewritable or not, or in the form of memory such as, for example, random access memory (RAM), memory chips, device or integrated circuits or on an optically or magnetically readable medium such as, for example, a compact disk (CD), digital versatile disc (DVD), magnetic disk or magnetic tape or the like. It will be appreciated that the storage devices and storage media are various embodiments of non-transitory machine-readable storage that are suitable for storing a computer program or computer programs comprising instructions that, when executed, implement various embodiments of the disclosure. Accordingly, various embodiments provide a program comprising code for implementing apparatus or a method as claimed in any one of the claims of this specification and a non-transitory machine-readable storage storing such a program.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A method of controlling an electronic apparatus, the method comprising:

based on a user touch for a first pulse wave sensor included in the electronic apparatus being detected, obtaining a first pulse wave signal through the first pulse wave sensor and receiving a second pulse wave signal detected through a second pulse wave sensor included in a wearable device from the wearable device;

removing noise of the first pulse wave signal and the second pulse wave signal using a band pass filter;

obtaining a cross-correlation signal indicating a correlation between denoised first pulse wave signal and the denoised second pulse wave signal;

authenticating a user based on the cross-correlation signal;

identifying a heart rate of the user based on the first pulse wave signal or the second pulse wave signal;

based on identifying that the heart rate of the user corresponding to the first pulse wave signal or the second pulse wave signal is equal to or less than a third threshold value or equal to or greater than a fourth threshold value, performing a face scan of the user using a camera of the electronic apparatus;

identifying whether the user is conscious based on the face scan; and based on identifying that the user is unconscious, maintaining a locked state of the electronic apparatus regardless of whether the user is authenticated, wherein the receiving of the second pulse wave signal comprises:

transmitting time stamp information corresponding to the first pulse wave signal and a signal for requesting the second pulse wave signal to the wearable device, wherein the second pulse wave signal is obtained based on time stamp information, and wherein the time stamp information includes a time after a predetermined time from a time when a user's touch is detected and a time when the first pulse wave signal begins to be obtained through the first pulse wave sensor.

2. The method of claim 1, wherein the authenticating of the user comprises, based on a peak value of the cross-correlation signal being equal to or greater than a first threshold value, authenticating the user.

3. The method of claim 2, wherein the authenticating of the user comprises, based on a deviation score being less than a second threshold value, authenticating the user.

4. The method of claim 1, further comprising:

obtaining a deviation score between the denoised first pulse wave signal and the denoised second pulse wave signal by comparing a peak-to-peak interval between the denoised first pulse wave signal and the denoised second pulse wave signal, a pulse interval or a systolic peak; and authenticating the user based on the deviation score.

5. The method of claim 1, further comprising:

identifying whether the user is in a sleeping state; and based on identifying that the user is in a sleeping state, maintaining a locked state of the electronic apparatus regardless of whether the user is authenticated.

6. The method of claim 1, further comprising:

based on user authentication being failed while the electronic apparatus is in an unlocked state, switching the electronic apparatus to a locked state.

7. The method of claim 1, further comprising:

obtaining fingerprint information of the user through a fingerprint sensor included in the electronic apparatus, wherein the authenticating the user comprises, based on the fingerprint information matching fingerprint information stored in the electronic apparatus and a peak value being equal to or greater than a first threshold value, authenticating the user.

8. The method of claim 1, further comprising:

identifying a user by comparing the first pulse wave signal or the second pulse wave signal with a third pulse wave signal stored in the electronic apparatus.

9. An electronic apparatus comprising:

a first pulse wave sensor;

a communication interface;

memory storing one or more computer programs; and one or more processors communicatively coupled to the first pulse wave sensor, the communication interface, and the memory, wherein the one or more computer programs include computer-executable instructions that, when executed by the one or more processors, cause the electronic apparatus to:

based on a user touch for the first pulse wave sensor being detected, obtain a first pulse wave signal through the first pulse wave sensor and receive a second pulse wave signal detected through a second pulse wave sensor included in a wearable device from the wearable device, remove noise of the first pulse wave signal and the second pulse wave signal using a band pass filter, obtain a cross-correlation signal indicating a correlation between denoised first pulse wave signal and the denoised second pulse wave signal, and authenticate a user based on the cross-correlation signal, identify a heart rate of the user based on the first pulse wave signal or the second pulse wave signal, based on identifying that the heart rate of the user corresponding to the first pulse wave signal or the second pulse wave signal is equal to or less than a third threshold value or equal to or greater than a fourth threshold value, perform a face scan of the user using a camera of the electronic apparatus, identify whether the user is conscious based on the face scan, and based on identifying that the user is unconscious, maintain a locked state of the electronic apparatus regardless of whether the user is authenticated, and wherein the one or more computer programs further include computer-executable instructions that, when executed by the one or more processors, cause the electronic apparatus to transmit time stamp information corresponding to the first pulse wave signal and a signal for requesting the second pulse wave signal to the wearable device, wherein the second pulse wave signal is obtained based on time stamp information, and wherein the time stamp information includes a time after a predetermined time from a time when a user's touch is detected and the time when the first pulse wave signal begins to be obtained through the first pulse wave sensor.

10. The electronic apparatus of claim 9, wherein the one or more computer programs further include computer-executable instructions that, when executed by the one or more processors, cause the electronic apparatus to, based on a peak value of the cross-correlation signal being equal to or greater than a first threshold value, authenticate the user.

11. The electronic apparatus of claim 9, wherein the one or more computer programs further include computer-executable instructions that, when executed by the one or more processors, cause the electronic apparatus to:

obtain a deviation score between the denoised first pulse wave signal and the denoised second pulse wave signal by comparing a peak-to-peak interval between the denoised first pulse wave signal and the denoised second pulse wave signal, a pulse interval or a systolic peak, and authenticate the user based on the deviation score.

12. The electronic apparatus of claim 11, wherein the one or more computer programs further include computer-executable instructions that, when executed by the one or more processors, cause the electronic apparatus to, based on the deviation score being less than a second threshold value, authenticate the user.

13. The electronic apparatus of claim 9, wherein the one or more computer programs further include computer-executable instructions that, when executed by the one or more processors, cause the electronic apparatus to:

identify whether the user is in a sleeping state, and based on identifying that the user is in a sleeping state, maintain a locked state of the electronic apparatus regardless of whether the user is authenticated.

14. The electronic apparatus of claim 9, wherein the one or more computer programs further include computer-executable instructions that, when executed by the one or more processors, cause the electronic apparatus to:

based on user authentication being failed while the electronic apparatus is in an unlocked state, switch the electronic apparatus to a locked state.

15. One or more non-transitory computer-readable storage media storing computer-executable instructions that, when executed by one or more processors of an electronic apparatus, cause the electronic apparatus to perform operations, the operations comprising:

based on a user touch for a first pulse wave sensor included in the electronic apparatus being detected, obtaining a first pulse wave signal through the first pulse wave sensor and receiving a second pulse wave signal detected through a second pulse wave sensor included in a electronic apparatus from a wearable device;

removing noise of the first pulse wave signal and the second pulse wave signal using a band pass filter;

obtaining a cross-correlation signal indicating a correlation between denoised first pulse wave signal and the denoised second pulse wave signal;

authenticating a user based on the cross-correlation signal;

identifying a heart rate of the user based on the first pulse wave signal or the second pulse wave signal;

based on identifying that the heart rate of the user corresponding to the first pulse wave signal or the second pulse wave signal is equal to or less than a third threshold value or equal to or greater than a fourth threshold value, performing a face scan of the user using a camera of the electronic apparatus;

identifying whether the user is conscious based on the face scan; and based on identifying that the user is unconscious, maintaining a locked state of the electronic apparatus regardless of whether the user is authenticated, wherein the receiving of the second pulse wave signal comprises:

transmitting time stamp information corresponding to the first pulse wave signal and a signal for requesting the second pulse wave signal to the wearable device, wherein the second pulse wave signal is obtained based on time stamp information, and wherein the time stamp information includes a time after a predetermined time from a time when a user's touch is detected and the time when the first pulse wave signal begins to be obtained through the first pulse wave sensor.

16. The one or more non-transitory computer-readable storage media of claim 15, wherein the authenticating of the user comprises, based on a peak value of the cross-correlation signal being equal to or greater than a first threshold value, authenticating the user.

* * * * *